US010221827B2

(12) United States Patent
Zhu et al.

(10) Patent No.: US 10,221,827 B2
(45) Date of Patent: Mar. 5, 2019

(54) IONIZATION DETECTOR WITH IGNITION COIL INDUCTANCE SHORTING

(71) Applicant: Board of Trustees of Michigan State University, East Lansing, MI (US)

(72) Inventors: Guoming G. Zhu, Novi, MI (US); Kevin D. Moran, Trenton, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 15/751,523

(22) PCT Filed: Aug. 11, 2016

(86) PCT No.: PCT/US2016/046505
§ 371 (c)(1),
(2) Date: Feb. 9, 2018

(87) PCT Pub. No.: WO2017/030889
PCT Pub. Date: Feb. 23, 2017

(65) Prior Publication Data
US 2018/0223791 A1 Aug. 9, 2018

Related U.S. Application Data

(60) Provisional application No. 62/205,022, filed on Aug. 14, 2015.

(51) Int. Cl.
*F02P 3/04* (2006.01)
*F02P 13/00* (2006.01)
(Continued)

(52) U.S. Cl.
CPC ............ *F02P 17/12* (2013.01); *F02D 35/021* (2013.01); *F02P 3/0435* (2013.01); *F02P 13/00* (2013.01);
(Continued)

(58) Field of Classification Search
CPC ....... F02P 17/12; F02P 3/0435; G01L 23/223; G01N 27/626
See application file for complete search history.

(56) References Cited

U.S. PATENT DOCUMENTS

| | | | |
|---|---|---|---|
| 2003/0021130 A1* | 1/2003 | Cohen | H02M 3/285 363/21.12 |
| 2004/0084035 A1 | 5/2004 | Newton | |
| 2005/0055169 A1* | 3/2005 | Zhu | F02P 17/00 702/64 |
| 2007/0137628 A1* | 6/2007 | Naruse | F02P 17/12 123/618 |
| 2009/0107457 A1 | 4/2009 | Meyer et al. | |

(Continued)

FOREIGN PATENT DOCUMENTS

| | | | | |
|---|---|---|---|---|
| DE | 19649278 A1 * | 6/1998 | ............. | F02P 17/12 |
| DE | 19649278 A1 * | 6/1998 | ............. | F02P 17/12 |
| DE | 19849258 A1 | 4/2000 | | |

OTHER PUBLICATIONS

Machine Translation of DE1996149278.*
(Continued)

*Primary Examiner* — Dedei K Hammond
*Assistant Examiner* — Raymond R Chai
(74) *Attorney, Agent, or Firm* — Harness, Dickey & Pierce, PLC

(57) ABSTRACT

An ionization detector that reduces the filtering effects of the ignition coil inductances by shorting an inductance of a primary winding of the ignition coil. The ionization detector includes a bias voltage source and an inductance control switch. The bias voltage source supplies electric voltage across an electric gap of a spark plug for detecting ionization within the combustion chamber. The inductance control (Continued)

switch is electrically parallel with a primary winding of an ignition coil and is operable to short an inductance of the primary winding.

18 Claims, 6 Drawing Sheets

(51) Int. Cl.
  *F02P 17/12* (2006.01)
  *F02D 35/02* (2006.01)
  *G01L 23/22* (2006.01)
  *G01N 27/62* (2006.01)
  *H01F 38/12* (2006.01)
  *H01T 13/58* (2011.01)
  *H01T 15/00* (2006.01)

(52) U.S. Cl.
  CPC .......... *G01L 23/223* (2013.01); *G01N 27/626* (2013.01); *F02P 2017/128* (2013.01); *H01F 38/12* (2013.01); *H01T 13/58* (2013.01); *H01T 15/00* (2013.01)

(56) References Cited

U.S. PATENT DOCUMENTS

| | | | |
|---|---|---|---|
| 2009/0241520 | A1 | 10/2009 | Gendron et al. |
| 2010/0077845 | A1* | 4/2010 | Pattantyus ............ F02D 35/021 73/114.67 |
| 2010/0186715 | A1* | 7/2010 | Aida ..................... F02D 35/021 123/406.28 |
| 2016/0160832 | A1* | 6/2016 | Skinner ................. F02P 3/0442 315/219 |

OTHER PUBLICATIONS

Machine Translation of DE19649278A1 (Year: 1998).*
Analysis of Electromagnetism in a Single-Phase Transformer, Jan. 26, 2016 from the internet http://www.iea.lth.se/emkrenew/exercises/EMK_task_2.pdf.

\* cited by examiner

# IONIZATION DETECTOR WITH IGNITION COIL INDUCTANCE SHORTING

CROSS-REFERENCE TO RELATED APPLICATIONS

This application is a National Phase Entry of International Patent Application No. PCT/US2016/046505, filed on Aug. 11, 2016, which claims the benefit of U.S. Provisional Application Ser. No. 62/205,022, filed on Aug. 14, 2015, which is incorporated by reference herein.

FIELD

The present disclosure relates to detecting ionization of gases in an internal combustion engine by measuring an ionization current through the secondary winding of a high-inductance ignition coil.

BACKGROUND

This section provides background information related to the present disclosure which is not necessarily prior art.

A spark ignition engine includes a spark plug that protrudes into a combustion chamber of the engine and provides an insulated electrode with a fixed spark gap to ground. An ignition coil provides the energy required for electrical current to arc across the spark gap igniting an air-fuel mixture within the combustion chamber and causing combustion.

During the combustion phase of the engine, heat and pressure cause ionization of gases within the combustion chamber. The degree of ionization is measured by applying a voltage across an electrical gap inside the combustion chamber and measuring the resulting current, which is referred to as an ionization current. The ionization current indicates the quality of the combustion, including the occurrence of knock and misfire. An engine control module analyzes a signal indicative of the ionization current and operates as part of a closed-loop combustion control to optimize the combustion within the chamber.

To detect the ionization current, an ionization detector utilizes the existing spark plug as the ionization sensing electrical gap inside the combustion chamber. However, the voltage at the spark plug terminal is extremely high during the spark event (e.g., 30 kV). Therefore, the ionization detector cannot be directly connected at the spark plug terminal. Instead, the ionization detector is connected to the spark plug by way of a secondary winding of the ignition coil.

The inductance characteristic of the second winding creates a parasitic low-pass filter, and effectively filters certain frequencies. A low energy ignition coil has a low enough secondary inductance to pass knock frequencies. However, the trend in automotive applications is toward higher energy coils that require higher inductance resulting in attenuation of the ionization signal, thereby preventing the engine control module from detecting the quality of the combustion, such as the occurrence of knock.

SUMMARY

The present disclosure relates to an ionization detector apparatus that detects ionization of gases. The ionization detector apparatus includes an ignition coil, a bias voltage source, and an inductance control switch. The ignition coil includes a primary winding and a secondary winding. The bias voltage source is electrically coupled to a secondary winding of the ignition coil and supplies electric voltage across an electrical gap by way of the secondary winding such that an ionization current flows across the electrical gap if ionized gas is present. The inductance control switch is positioned electrically parallel with the primary winding of the ignition coil and is operable to short an inductance of the primary winding.

The ionization detector of the present disclosure is advantageous over conventional devices. For example, by shorting the inductance of the primary winding, the ionization detector reduces a secondary impedance of the ignition coil. Accordingly, the ionization detector reduces the filtering effects that the ignition coil has on the ionization signal such that frequencies from DC through the knock frequency are passed by the ignition coil. Further areas of applicability will become apparent from the description provided herein. The description and specific examples in this summary are intended for purposes of illustration only, and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

An ionization detector used to detect ionization of gases in an internal combustion engine detects an ionization current that flows across a spark plug. By routing the ionization current through a secondary winding of an ignition coil, a first order low-pass filter is created between the ionization detector and the spark plug causing attenuation of an ionization signal that is indicative of the ionization current.

An ionization detector of the present disclosure is configured to short an inductance of the ignition coil during a combustion phase of the engine. More particularly, the ionization detector shorts the inductance of the primary winding to effectively reduce the impedance of the secondary winding and therefore, reduces the attenuation of the ionization signal.

Figure 1A:
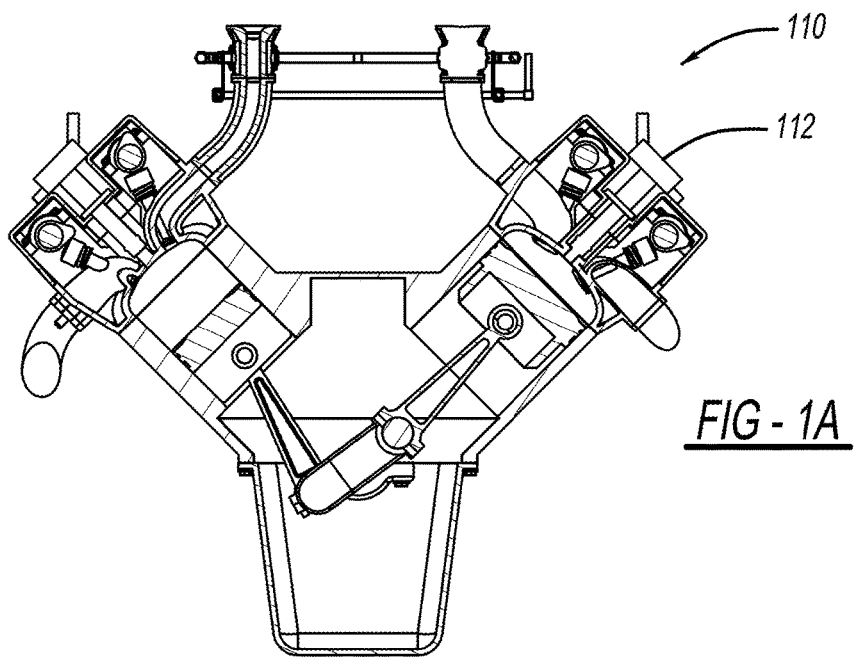
FIGS. 1A and 1B illustrate a spark-ignition system including a spark ignition device for an internal combustion engine.
Figure 1B:
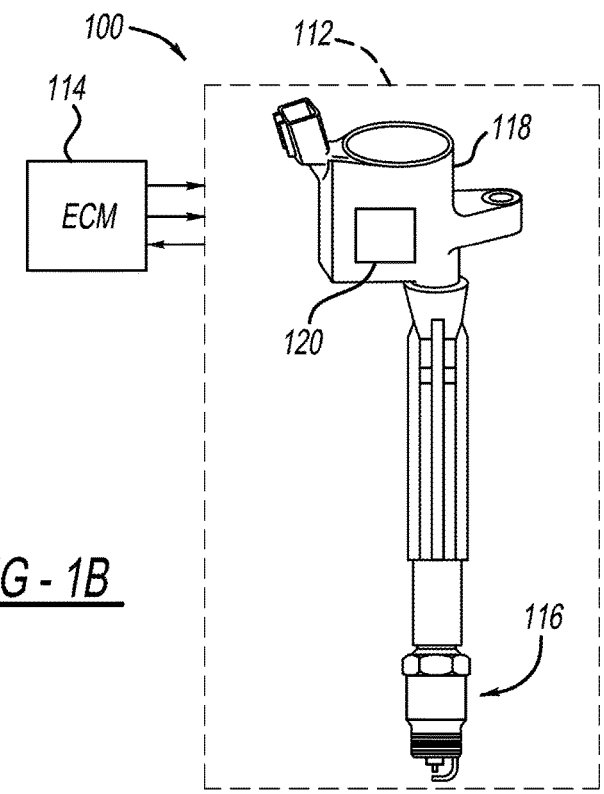

The present disclosure will now be described with reference to the accompanying drawings. FIGS. 1A and 1B illustrate a spark-ignition system 100 for an internal combustion engine 110 application. The spark-ignition system 100 includes a spark ignition device 112 and an engine control module (ECM) 114 that controls the operation of the spark ignition device 112. The ECM 114 includes an integrated circuit with a processor and a memory that stores code to be executed by the processor. The ECM 114 is in communication with the spark ignition device 112 to control components within the spark ignition device 112 during an ignition and combustion cycle. As part of a closed-loop control system, the ECM 114 receives data from the spark ignition device 112 and uses such data to optimize the timing of the spark event within a combustion chamber of the engine 110.

The spark ignition device 112 protrudes into the combustion chamber of the engine 110 to ignite an air-fuel mixture within the combustion chamber. The spark ignition device 112 includes a spark plug 116, an ignition coil 118, and an ionization detector 120. The ionization detector 120 is illustrated as being integrated with the ignition coil 118, but does not necessarily need to be integrated with the ignition coil 118. The spark plug 116 protrudes in the combustion chamber, and the ignition coil 118 generates the necessary voltage for creating an electric spark in the spark plug 116 to ignite the air-fuel mixture. The ionization detector 120 utilizes the spark plug 116 to detect ionization of gases within the chamber during combustion.

Figure 2:
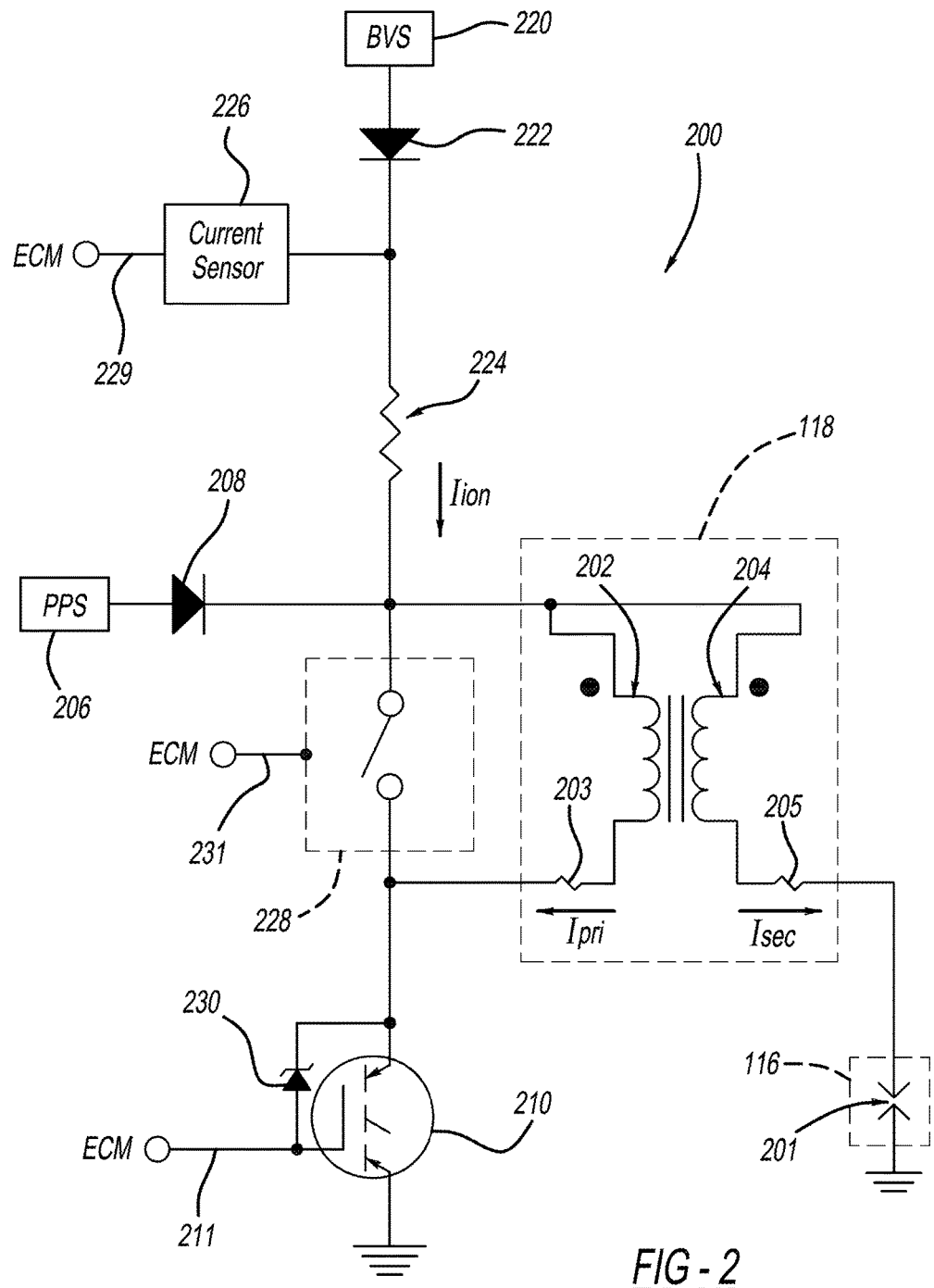
FIG. 2 is a circuit diagram of the spark ignition device in a first embodiment of the present disclosure.

FIG. 2 illustrates a circuit diagram 200 of the spark ignition device 112 in a first embodiment of the present disclosure. The ignition coil 118 is a flyback transformer and includes a primary winding 202 and a secondary winding 204 wound around a common magnetic core. The ignition coil 118 has a high secondary-to-primary turn ratio for generating the voltage required for current to arc across a spark gap 201 of the spark plug 116. As an example, the secondary-to-primary turn ratio (N) is equal to: $N=n_{sec}/n_{pri}=80$. The primary winding 202 and the secondary winding 204 have a winding resistance represented by resistors 203 and 205, respectively. Due to the high secondary-to-primary turn ratio, the winding resistance of the secondary winding 204 is greater than the winding resistance of the primary winding 202.

The primary winding 202 is disposed between a primary power source (PPS) 206 and ground. Specifically, one terminal of the primary winding 202 is electrically coupled to the primary power source 206 by way of a diode 208. The other terminal of the primary winding 202 is electrically coupled to ground by way of a primary switch 210. The primary switch 210 is typically an insulated-gate bipolar transistor (IGBT) that is controlled by the ECM 114. More particularly, the ECM 114 transmits a signal to the primary switch 210, as represented by transmission line 211, to turn the IGBT ON and OFF. In the OFF state, the IGBT performs as an open switch and, in the ON state, the IGBT performs as a closed switch.

The secondary winding 204 is disposed between the spark plug 116 and a power source of the ionization detector 120. Specifically, one end of the secondary winding 204 is electrically coupled in series with spark plug 116 and ground. The other end of secondary winding 204 is electrically coupled to the primary power source 206 by way of a diode 208 during spark dwell and ignition, and to a bias voltage source (BVS) 220 by way of a diode 222 and a resistor 224 when high dwell and spark currents are not flowing.

The bias voltage source 220 is a power source for ionization detection, as described further below. The bias voltage source 220 supplies more voltage to the circuit 200 than the primary power supply 206. As an example, the bias voltage source 220 supplies 100V, whereas the primary power source 206 supplies the engine's electrical system voltage, typically on the order of 15V. The primary power source 206 is the application system voltage which is typically a low voltage battery and charging system, and the bias voltage source 220 is provided as power from a boost converter that increases voltage from the application's system voltage to the necessary voltage for ionization detection.

In addition to the bias voltage source 220, the ionization detector 120 includes a current sensor 226 and an inductance control switch 228. The current sensor 226 measures an ionization current ($I_{ion}$) flowing from the bias voltage source 220 to the spark plug 116. The current sensor 226 communicates with the ECM 114 as represented by transmission line 229, and transmits a signal indicative of the ionization current to the ECM 114. The current sensor 226 monitors the ionization current by measuring the current through resistor 224.

The inductance control switch 228 is disposed in parallel with the primary winding 202. The ECM 114 controls the state of the inductance control switch 228, such that the switch 228 is either open or closed. Specifically, the ECM 11 transmits a signal to the inductance control switch, as represented by transmission line 231, to open or close the switch 228. When the inductance control switch 228 is closed, the switch 228 creates a short across the primary winding 202, thereby shorting the inductance of the primary winding 202. As described further below, the inductance control switch 228 reduces filtering effects of the ignition coil 118 during ionization detection.

The ECM 114 controls the operation of the spark ignition device 112 by way of the primary switch 210 and the inductance control switch 228. More particularly, the spark ignition device 112 is operable in four modes: inactive mode, dwell mode, spark mode, and combustion mode. In the inactive mode, the primary switch 210 and the inductance control switch 228 are open, such that no current is flowing through the circuit 200. The voltage at the positive and negative terminals of the primary winding 202 ($V_{pri}(+)$, $V_{pri}(-)$) is approximately equal to the voltage of the bias voltage source 220 ($V_{bias}$; $V_{bias}=V_{pri}(+)=V_{pri}(-)$). Since the voltage of the bias voltage source 220 is greater than the voltage of the primary power source 206, the diode 208 is reverse biased.

In the dwell mode, the ECM 114 applies a signal to the primary switch 210 to close the primary switch 210 and connect the primary winding 202 to ground. Once closed, the diode 208 forward biases and current begins to flow from the primary power source 206 through the primary winding 202 to ground increasing at a rate described in equation (1). As current flows through the primary switch 210, energy in the magnetic gap between the primary winding 202 and the secondary winding 204 increases and is estimated by equation (2), where $L_{pri}$ is the inductance of the primary winding 202. The current through the primary winding 202 is identified as $I_{pri}$ and is also referred to as the primary winding current. The primary winding current is in the order of amps.

$$\frac{dI_{pri}}{dt} = \frac{V_{pri}}{L_{pri}} \qquad (1)$$

$$E = \frac{1}{2}L_{pri}I_{pri}^2 \qquad (2)$$

A zener diode 230 provided with the primary switch 210 clamps a primary flyback voltage that is released when the dwell mode is completed. After the dwell mode, the ECM 114 proceeds to the spark mode in which the ECM 114 discontinues the signal to the primary switch 210, thereby opening the primary switch 210 and discontinuing the primary winding current. The diode 208 continues to conduct holding the voltage at the positive terminal of the primary winding at: $V_{pri}(+)=V_{pwr}-V_{D1}$, where $V_{pwr}$ is the voltage of the primary power source 206 and $V_{D1}$ is the voltage drop across the diode 208. The voltage at the negative terminal of the primary winding 202 flies up to a clamp voltage, which is of higher magnitude than the voltage supplied by the primary power source 206. In the example embodiment, the clamp voltage is 500V. Energy is released to the secondary winding 204, such that current begins to flow and arcs across the spark gap 201 of the spark plug 116. The voltage at the negative terminal of the primary winding 202 remains at the clamp voltage until a coil leakage inductance is depleted and current through the primary winding 202 ceases to flow.

In the combustion mode, the spark event has ignited the air-fuel mixture in the combustion chamber and ionization of the gases occurs. The diode 208 is reverse biased, the primary switch 210 remains open, and all energy stored in the ignition coil 118 is depleted.

To measure the ionization of the gases in the combustion chamber, the ECM 114 performs an ionization detection by way of the ionization detector 120. Specifically, the ECM 114 closes the inductance control switch 228 to short the inductance ($L_{mag}$) of the primary winding 202. The ionization current flows from the bias voltage source 220 through resistor 224, through the secondary winding 204 and across the spark gap 201. The ionization current is equal to the current flowing through the secondary winding 204 ($I_{sec}$; $I_{ion}=I_{sec}$). The current flowing through secondary winding 204 is also referred to as secondary winding current.

Figure 3:
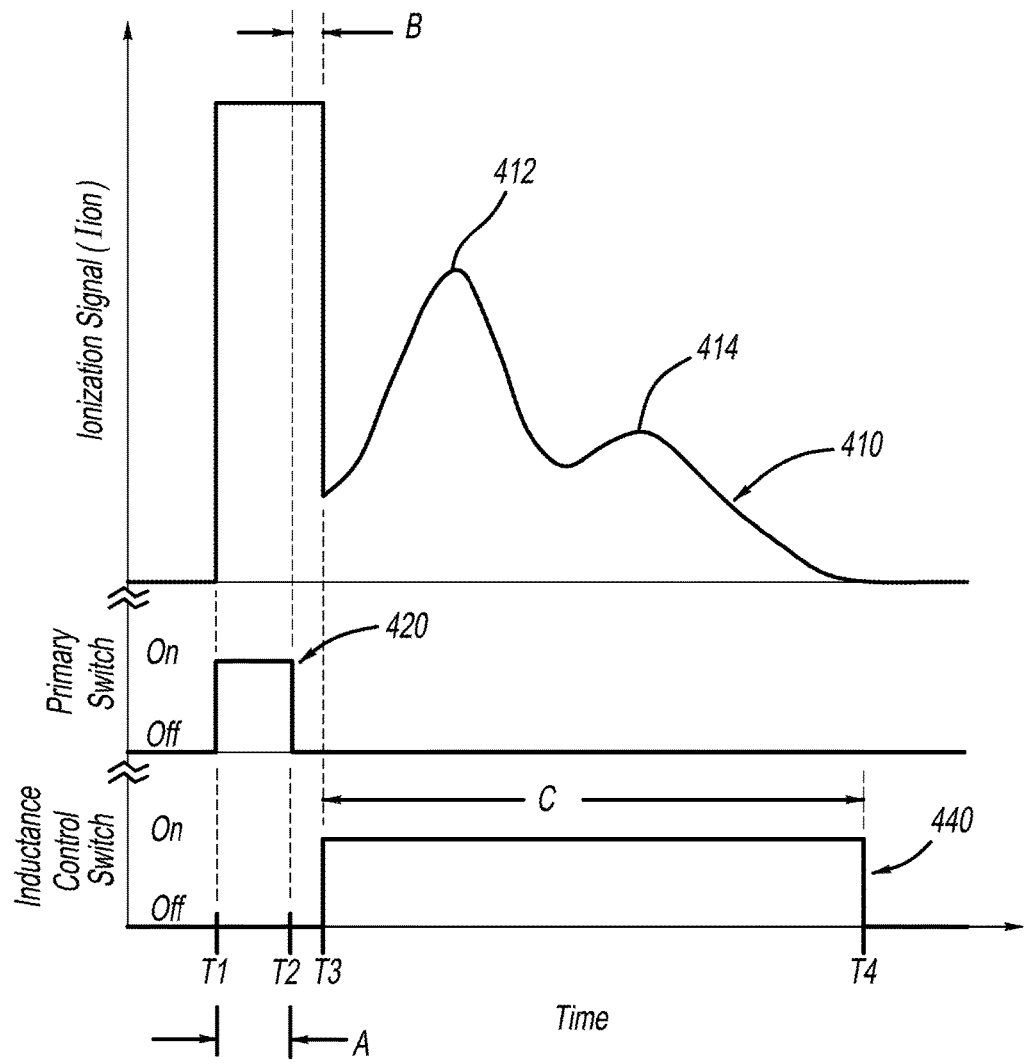
FIG. 3 is a graph illustrating an ionization signal, a dwell control signal, and a short control signal for a spark-combustion cycle.

FIG. 3 illustrates a prophetic graph of a spark-combustion cycle that includes the dwell mode, the spark mode, and the combustion mode. The graph associates an ionization current measurement signal 410 taken by the ionization detector 120 with a dwell control signal 420 and a short control signal 440 provided to the primary switch 210 and the inductance control switch 228 by the ECM 114, respectively. In the graph, time period A, which is between T1 and T2, represents the dwell mode in which a high level signal is provided to the primary switch 210 from the ECM 114. Time period B, which is between T2 and T3, is the spark mode in which the high level signal is discontinued. During the dwell mode and spark mode, the inductance control switch 228 remains open (i.e., OFF-state), as indicated by the low level of the short control signal 440. In addition, the diode 208 is forward biased and a maximum ionization current is determined in equation (3):

$$\overline{I_{ion}} = \frac{V_{bias} - V_{pwr} - V_{D1}}{R1} \quad (3)$$

After the spark mode, the combustion mode is initiated in time period C, which is between T3 and T4. The short control signal 440 goes from low to high to turn ON the inductance control switch 228, such that the switch 228 is in a closed state to form the short across the primary winding 202. As combustion begins, the flame front is in and near the spark gap 201. This high degree of localized ionization results in a first hump 412 in the ionization current signal 410. As the flame front moves away from the spark plug 116 expanding throughout the volume of the combustion chamber, a second hump 414 develops. The second hump 414 peak coincides with the peak pressure in the combustion chamber. If knock is present in the combustion, it will appear as an oscillation wave riding on the descending slope of the second hump 414.

Figure 4A:
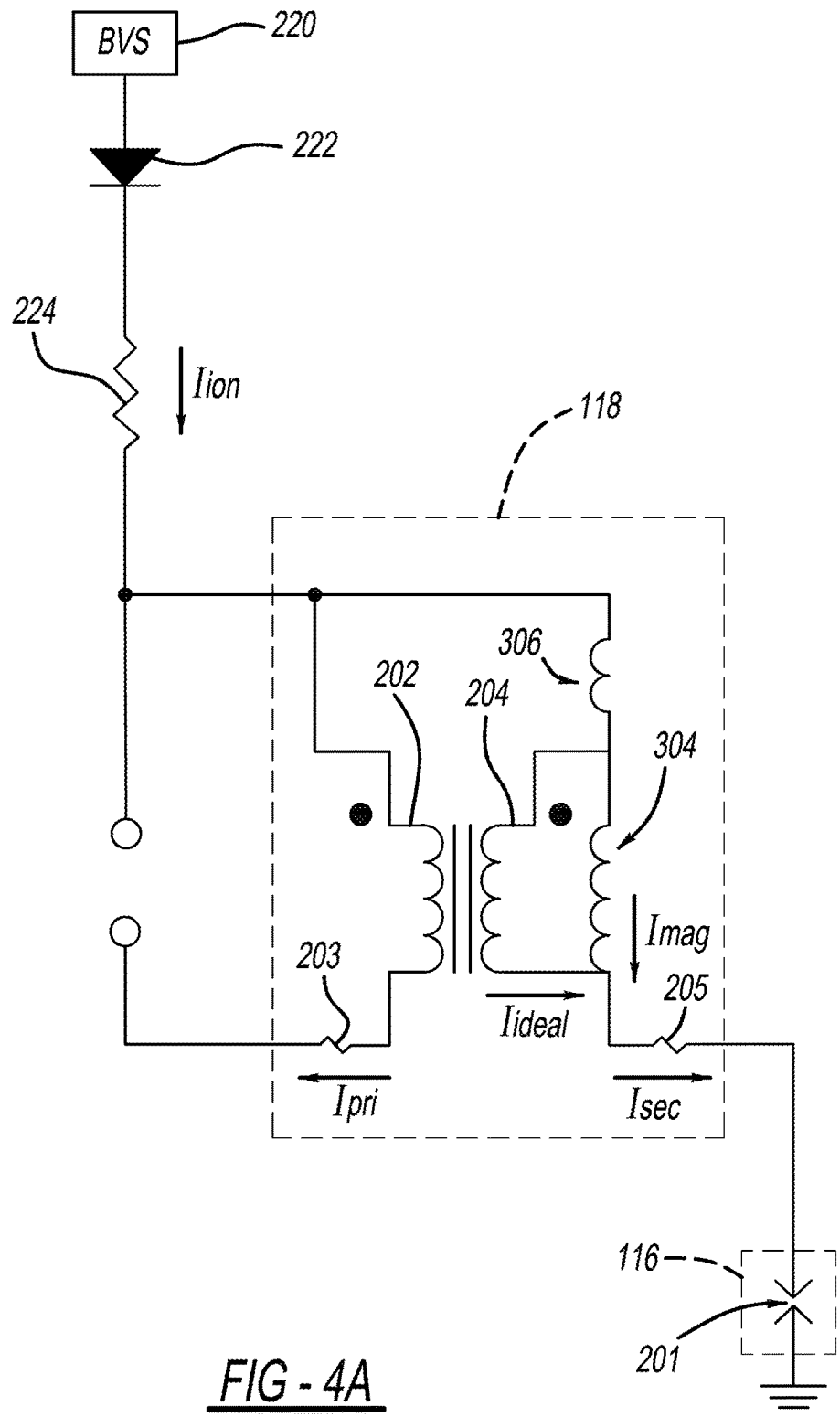
FIG. 4A is a transformer model of an ignition coil of the spark ignition device without a short across a primary winding of the ignition coil.
Figure 4B:
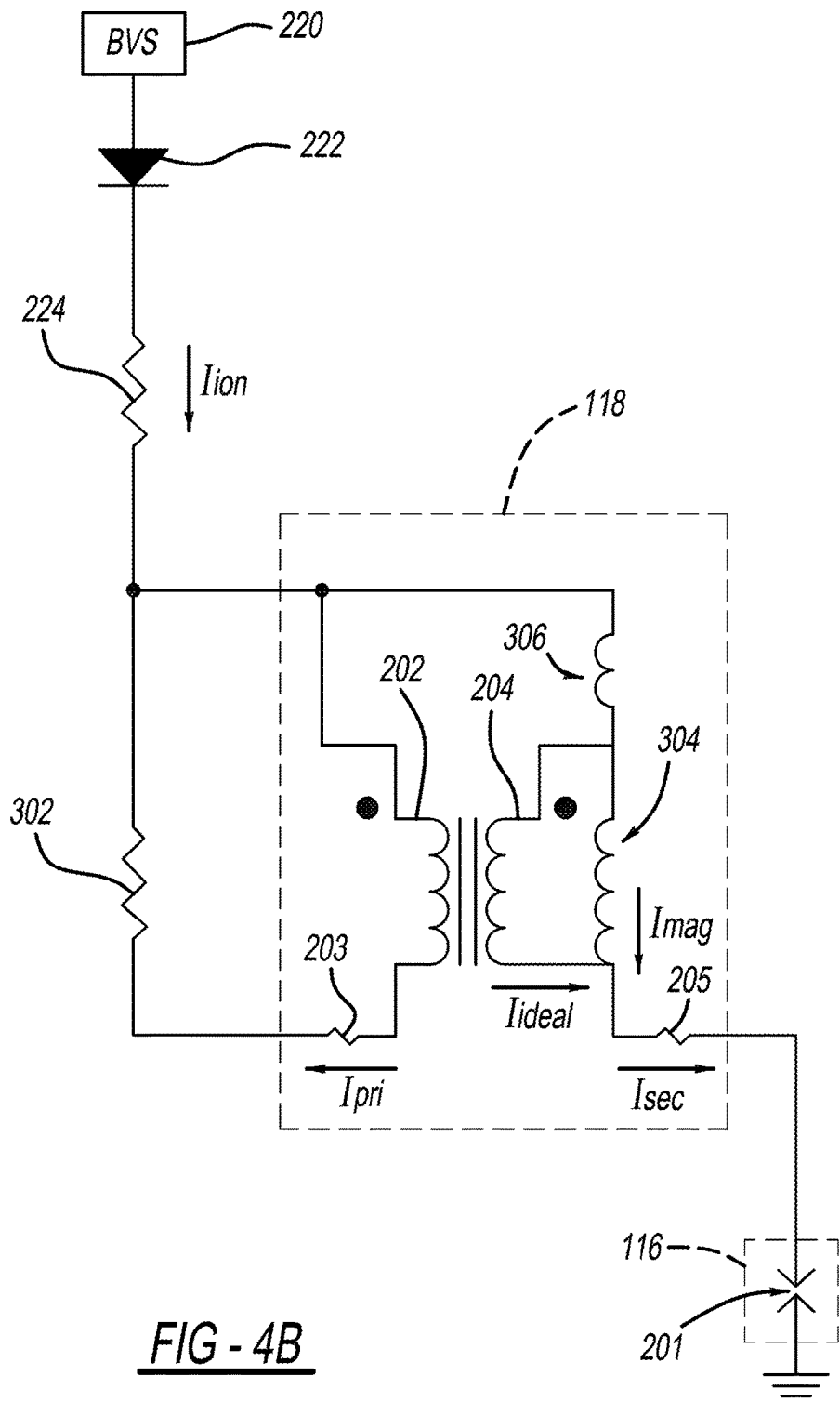
FIG. 4B is a transformer model of the ignition coil of the spark ignition device with a short across the primary winding of the ignition coil.

To understand the effect of the short across the primary winding 202, FIGS. 4A and 4B illustrate transformer models of the ignition coil 118 when the inductance control switch 228 is open and closed, respectively. In FIG. 4B, a resistor 302 represents the resistance provided by the closed inductance control switch 228 and has a much smaller resistance than the resistor 224. The resistor 302 could be non-linear.

The transformer is modeled with an ideal turns ratio of 1:N, a magnetizing inductance ($L_{mag}$), leakage inductance ($L_{leak}$), and two winding resistances illustrated as the resistors 203 and 205. Equations (4) and (5) reflect current and voltage relationships for the ideal transformer action. In equations (4) and (5), $I_{ideal}$ is the ideal turns current of the secondary winding, $R_{pri}$ and $R_{sec}$ are the resistances of the primary winding 202 (resistor 203) and the secondary winding (resistor 205), respectively, $R_{sw(ON)}$ is the resistance of the short (i.e., resistor 302), and $V_{sec}$ is the voltage at the negative terminal of the secondary winding 204.

$$I_{pri} = I_{ideal} * N \quad (4)$$

$$V_{pri(+)} - V_{sec} = I_{ideal} * (R_{pri} + R_{sw(on)}) * N^2 + I_{sec} * R_{sec} \quad (5)$$

With the inductance control switch 228 open, there is no continuous path through the primary winding 202 for supporting an electric current. That is, the ideal current ($I_{ideal}$) cannot flow, thereby causing a magnetizing current ($I_{mag}$) to be equal to the ionization current. The ionization current is frequency limited by the inductance of the secondary winding 204, which is equal to the sum of a magnetizing inductance ($L_{mag}$) and the leakage inductance ($L_{leak}$). The magnetizing inductance and the leakage inductance are represented as windings 304 and 306, respectively, in FIGS. 4A and 4B.

With the inductance control switch 228 closed, a loop is created with the primary winding 202. Specifically, the inductances of the primary winding 202 and the secondary winding 204 are related by the turns ratio as provided in equation (6). Since the inductance control switch 228 shorts the inductance of the primary winding 202, the inductance of the secondary winding 204 is in return shorted by the primary winding 202.

$$L_{sec} = L_{pri} * N^2 \quad (6)$$

More particularly, with only one common node, the primary winding current is independent of the ionization current and the secondary winding current. When the magnetic energy of the transformer is depleted and a step occurs in the ionization current from zero to a positive value, the ionization current flows through the secondary winding 204 causing the magnetizing current to increase. The magnetizing current continues to increase with the ideal current and the primary winding current decreasing. Thus, shorting the primary winding effectively shunts the current that would otherwise be restricted by the magnetizing inductance.

Figure 5:
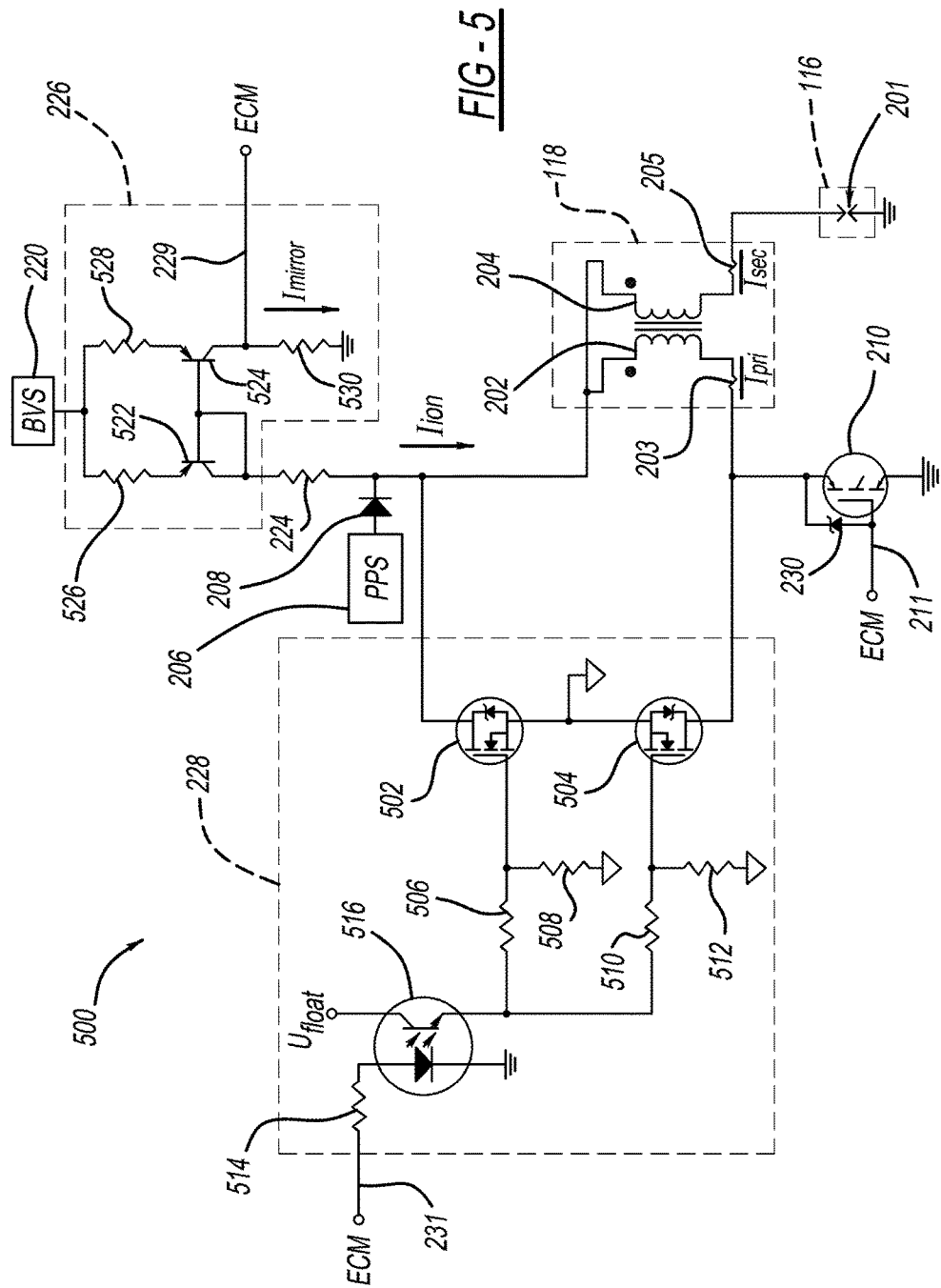
FIG. 5 is a circuit diagram of the spark ignition device in a second embodiment of the present disclosure.

FIG. 5 illustrates a circuit diagram 500 for the spark ignition device 112 in a second embodiment of the present disclosure. In the second embodiment, the inductance control switch 228 comprises transistors 502 and 504, resistors 506, 508, 510, 512, and 514, and a driver 516. The transistors 502 and 504 are metal-oxide-semiconductor field-effect transistors (MOSFETs). The transistors 502 and 504 have a higher breakdown voltage than the primary switch 210.

The drain of transistor 502 is electrically coupled to the positive terminal of the primary winding 202, and the drain of transistor 504 is electrically coupled to the negative terminal of the primary winding 202. The gates of the transistors 502 and 504 are electrically coupled to a floating voltage source ($V_{float}$) by way of the driver 516 and resistors 506, 508, 510, and 512. The sources of the transistors 502 and 504 are electrically coupled to the ground of the floating voltage source. The transistors 502 and 504 are ON when electric power is applied to the gates and are OFF when no electric power is applied to the gates. In the ON state, the transistors 502 and 504 allow current to flow between the source and the drain and, therefore, perform as a closed switch as described further below. The resistances of resistors 506, 508, 510 and 512 are selected to maximize the voltage across the transistors 502 and 504 in order to minimize the resistance between the drain and the source when transistors 502 and 504 receive power.

The driver 516 is an opto-isolator and is controlled by the ECM 114. Specifically, the ECM 114 transmits the short control signal to the driver 516, as represented by transmission line 231. When the signal is high, the opto-isolator conducts and current flows from the floating voltage source to the gates of transistors 502 and 504.

In the second embodiment, the current sensor 226 includes a current mirror circuit that isolates the ionization current to a mirrored current ($I_{mirror}$) that is proportional to the ionization current. The current sensor 226 outputs a signal indicative of the ionization current to the ECM 114, as represented by transmission line 229. The current sensor 226 includes transistors 522 and 524 and resistors 526, 528, and 530. The transistors 522 and 524 are pnp-type bipolar junction transistors (BJT) in this embodiment, but could also be other types of transistors such as Field Effect Transistors (FET).

During operation of the current mirror circuit, the ionization current flows through resistor 526, transistor 522, and resistor 224. Using matched transistors 522 and 524, the ionization current is mirrored or, in other words, copied to also flow in resistor 528, transistor 524, and resistor 530. The transistors 522 and 524 have as high of a gain as possible to minimize current mirror error. The mirrored current is equal to: $I_{ion}*R_{526}/R_{528}$, where $R_{526}$ is the resistance of resistor 526 and $R_{528}$ is the resistance of resistor 528. The resistor 530 converts the mirrored current into a voltage that is indicative of the ionization voltage ($V_{ion}$).

During the dwell mode and the spark mode, transistors 502 and 504 remain off. Specifically, the short control signal remains low and no current is flowing from the driver 516. In the dwell mode, the positive terminal of the primary winding 202, which is electrically coupled to the drain of transistor 502, is positive. The body diode of transistor 502 is reverse biased and below the avalanche voltage, thereby protecting the body diode of transistor 504 from forward conducting. At the conclusion of dwell, the dwell current is shut off and the primary winding voltage experiences a very large negative flyback voltage as described in equation (1) and clamped by the zener diode of transistor 230. This causes the negative terminal of the primary winding 203 to become positive and the body diode 541 of transistor 504 is reverse biased below the avalanche voltage, thereby protecting the body diode 540 of transistor 502 from forward conducting.

During the combustion mode, the spark event has ignited the air-fuel mixture in the combustion chamber and ionization of the gases occurs. As stated above, the primary switch 210 is open (i.e., OFF-state) and all energy stored in the ignition coil 118 during the dwell mode is depleted. The voltage applied across the spark plug 116 is equal to the voltage of the bias voltage source 220 minus the PN junction drop of transistor 522 and the drop across all series resistances.

The short control signal is high, such that the opto-isolator (i.e., driver 516) conducts. Current flows through resistors 506, 508, 510, and 512 turning on transistors 502 and 504. With the transistors 502 and 504 ON, a short is formed across the primary winding 202.

Similar to the circuit 200 of the first embodiment, the circuit 500 shorts the inductance of the primary winding to effectively reduce the secondary impedance of the ignition coil. Accordingly, the ionization detector 120 reduces the filtering effects that the ignition coil has on the ionization signal such that frequencies from DC through the knock frequency (e.g., 12 kHz) are passed by the ignition coil.

The foregoing description of the embodiments has been provided for purposes of illustration and description. It is not intended to be exhaustive or to limit the disclosure. For example, the bias voltage source may be a separate battery. Furthermore, the floating power source may be a forward-mode transformer circuit with a pulse width modulated input. Additionally, an integrated circuit designed to drive the MOSFET gates can be added between the opto-isolator and the MOSFET gates to improve the switching time of the inductance control switch. Furthermore, the secondary-to-primary turn ratio can be a different value and is not limited to 80. The present disclosure may be applied in various applications that include an internal combustion engine, such as a vehicle, a stationary generator, and/or other suitable engine system. The ionization detector may be implemented in various ways. For example, the detector may be: integrated into the ignition coil; located disposed externally using a two pin coil, where the primary and secondary windings have an internal connection; or located externally using a three pin coil with an isolated secondary winding. Individual elements or features of a particular embodiment are generally not limited to that particular embodiment but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An ionization detector apparatus for detecting ionization of gases, the apparatus comprising:
    a coil having a primary winding and a secondary winding;
    a bias voltage source electrically coupled to the secondary winding, wherein the bias voltage source supplies electric voltage across an electrical gap by way of the secondary winding such that an ionization current flows across the electrical gap in response to ionized gas being present;
    an inductance control switch positioned electrically parallel with the primary winding of the coil and operable to short an inductance of the primary winding, wherein the inductance control switch includes a plurality of transistors; and
    a current sensor outputting a signal indicative of the ionization current flowing from the bias voltage source to the electrical gap, wherein the current sensor comprises a current mirror circuit.

2. The ionization detector apparatus of claim 1 wherein:
the inductance control switch includes a driver;
the plurality of transistors are electrically coupled between a positive terminal and a negative terminal of the primary winding; and
the driver is operable to drive the plurality of transistors to an ON state or an OFF state such that the inductance control switch shorts the inductance of the primary winding when the transistors are in the ON state.

3. The ionization detector apparatus of claim 2 wherein:
the plurality of transistors includes a first transistor and a second transistor, both the first transistor and the second transistor have a gate, a drain, and a source;
the gates of the first transistor and the second transistor are electrically coupled to the driver;
the drain of the first transistor is electrically coupled to the positive terminal of the primary winding;
the drain of the second transistor is electrically coupled to the negative terminal of the primary winding; and
the sources of the first transistor and the second transistor are electrically coupled to a common ground.

4. The ionization detector apparatus of claim 1 wherein the plurality of transistors of the inductance control switch are a plurality of metal-oxide-semiconductor field-effect transistors electrically coupled between a positive terminal and a negative terminal of the primary winding.

5. The ionization detector apparatus of claim 4 further comprising a driver operable to drive the plurality of metal-oxide-semiconductor field-effect transistors to an ON state or an OFF state such that the inductance control switch shorts the inductance of the primary winding when the metal-oxide-semiconductor field-effect transistors are in the ON state.

6. The ionization detector apparatus of claim 1 wherein the inductance control switch shorts the inductance of the primary winding after a high voltage spark event across the electrical gap.

7. The ionization detector apparatus of claim 1 wherein the plurality of transistors of the inductance control switch are two metal-oxide-semiconductor field-effect transistors with common source terminals and electrically coupled between a positive terminal and a negative terminal of the primary winding to short the inductance of the primary winding.

8. The ionization detector apparatus of claim 1 further comprising:
a spark plug having the electrical gap, wherein the spark plug is operable to ignite gas, and the inductance control switch shorts the inductance of the primary winding after the spark plug ignites gas.

9. A spark-ignition system comprising:
a spark plug having an electrical gap and operable to generate an electric spark for igniting gas;
an ignition coil including a primary winding and a secondary winding, wherein the ignition coil is operable to generate an electric current that arcs across the electrical gap of the spark plug to generate the electric spark;
an ionization detector sensing an ionization current after gases are ignited and including a bias voltage source and an inductance control switch, wherein the bias voltage source is electrically coupled to the secondary winding of the ignition coil and the inductance control switch is electrically parallel with the primary winding and is operable to short an inductance of the ignition coil, and wherein the inductance control switch includes a plurality of transistors; and
a current sensor outputting a signal indicative of the ionization current flowing from the bias voltage source to the electrical gap, wherein the current sensor comprises a current mirror circuit.

10. The spark-ignition system of claim 9 wherein the spark plug is electrically coupled to the secondary winding of the ignition coil such that the secondary winding is disposed between the bias voltage source and the spark plug.

11. The spark-ignition system of claim 9 further comprising:
a primary power source different from the bias voltage source and electrically coupled to the primary winding;
a primary switch electrically coupled between the primary winding of the ignition coil and ground to control flow of electric current through the primary winding from the primary power source; and
an engine control module controlling a state of the primary switch and the inductance control switch of the ionization detector.

12. The spark-ignition system of claim 11 wherein:
the engine control module, during a dwell mode, controls the primary switch to a closed state to have electric current flow through the primary winding of the ignition coil from the primary power source and controls the inductance control switch to an open state;
the engine control module, during a spark mode, controls the primary switch to the open state and controls the inductance control switch to the open state; and
the engine control module, during a combustion mode, controls the primary switch to the open state and controls the inductance control switch to the closed state such that an inductance of the primary winding is shorted.

13. The spark-ignition system of claim 9 wherein the plurality of transistors of the inductance control switch are two transistors electrically coupled with common source terminal and electrically coupled across terminals of the primary winding of the ignition coil.

14. The spark-ignition system of claim 13 wherein the inductance control switch further includes a driver that is operable to drive the transistors.

15. The spark-ignition system of claim 9 wherein the ionization detector is integrated with the ignition coil.

16. The spark-ignition system of claim 9 wherein the ignition coil is a two pin coil in which the primary and secondary windings have an internal connection, and the ionization detector is located externally of and electrically coupled to the ignition coil.

17. The spark-ignition system of claim 9 wherein the ignition coil is a three pin coil with an isolated secondary winding, and the ionization detector is located externally of and electrically coupled to the ignition coil.

18. A method for operating a spark-ignition system, the method comprising:
building magnetic energy between a primary winding and a secondary winding of an ignition coil;
releasing the magnetic energy through the secondary winding such that an electric current arcs across an electrical gap of a spark plug to ignite an air-fuel mixture;
shorting an inductance of the ignition coil after the air-fuel mixture is ignited by activating a plurality of transistors positioned electrically parallel with the primary winding of the ignition coil such that the transistors short an inductance of the primary winding;
measuring an ionization current flowing from a bias voltage source to the spark plug, wherein the bias voltage source is electrically coupled to the spark plug by way of the secondary winding such that the secondary winding is disposed between the spark plug and the bias voltage source; and outputting a signal indicative of the ionization current flowing from the bias voltage source to the electrical gap.

\* \* \* \* \*